United States Patent [19]

Baldwin

[11] Patent Number: 4,666,835
[45] Date of Patent: May 19, 1987

[54] 2-VINYLPENAMS AND PROCESS

[76] Inventor: Jack E. Baldwin, 10 Rolfe Place, Headington, Oxford, England

[21] Appl. No.: 856,997

[22] Filed: Apr. 29, 1986

[51] Int. Cl.$^4$ .................... C12P 37/00; C07D 499/42; C07D 499/46
[52] U.S. Cl. ..................................... 435/43; 540/312; 540/314; 540/328
[58] Field of Search ..................... 260/245.2 R, 239.1; 435/43; 540/312, 314, 328

[56] References Cited

U.S. PATENT DOCUMENTS 3,499,909  3/1970  Wiessenburger et al. ... 260/245.2 R
4,044,000  8/1977  Koppel ........................... 260/239.1
4,539,149  9/1985  Milner ............................. 260/239.1

OTHER PUBLICATIONS

Pang et al., Biochem. J. (1984), 222, 789–795, "Purification of Isopenicillin N Synthetase".
Baldwin et al., FEBS Letters, 1985, 188, 253–256.
Bartlett et al., J. Org. Chem., 1982, 47, 3933–3941, "Ester-Enolate Claisen Rearrangement of Alpha-Amino Acid Derivatives".
Baldwin et al., J. Chem. Soc., Perkin I, 1981, 2253.
Baldwin et al., J. Chem. Soc., Chem. Commun., 1986, 273–275.
Baldwin et al., J. Chem. Soc., Chem. Commun., 1984, 1211–1214.

Primary Examiner—Natalie Trousof
Assistant Examiner—Vera C. Clarke
Attorney, Agent, or Firm—William B. Scanlon; Leroy Whitaker

[57]   ABSTRACT

6$\beta$-(L-$\alpha$-Aminoadipoyl)-2$\alpha$-vinyl-2$\beta$-methylpenam-3-carboxylic acid is provided in an enzymatic process converting $\delta$-(L-$\alpha$-aminoadipoyl)-L-cysteinyl-D-$\gamma$,$\delta$-didehydroisoleucine with isopenicillin N synthetase. The 2$\alpha$-vinylpenam product is converted by known methods to the 6$\beta$-amino-2$\alpha$-vinyl-2$\beta$-methylpenam-3-carboxylic acid nucleus and the latter is N-acylated to provide corresponding 6$\beta$-acylaminopenams.

14 Claims, No Drawings

2-VINYLPENAMS AND PROCESS

BACKGROUND OF THE INVENTION

This invention relates to a process for preparing novel penicillins and to penicillin antibiotic compounds. In particular, it relates to an enzymatic process for converting an N-terminal vinyl-substituted tripeptide to a 2-methyl-2-vinylpenam with isopenicillin N synthetase and to 6-acylamino-2-methyl-2-vinylpenam-4-carboxylic acids prepared with the product of the process.

The enzyme isopenicillin N synthetase is well known for its ability to cyclize the tripeptide δ-(L-α-aminoadipoyl)-L-cysteinyl-D-valine to isopenicillin N. The enzyme is obtained from numerous sources such as *Penicillium chrysogenum, Cephalosporium acremonium* and *Streptomyces clavuligerus* cultures and is used as a cell-free extract. Because of the importance of the penicillins and other β-lactam antibiotics in therapy, considerable effort has been undertaken to explore the use of this synthetase in the preparation of β-lactam compounds. As described herein, the isopenicillin N synthetase is employed in a process for converting an N-terminal vinyl-substituted tripeptide to a 2-methyl-2-vinylpenam.

SUMMARY

The tripeptide δ-(L-α-aminoadipoyl)-L-cysteinyl-D-γ,δ-didehydroisoleucine is incubated with isopenicillin N synthetase in the presence of ferrous ion and oxygen to provide 6β-(L-α-aminoadipoylamino)-2β-methyl-2α-vinylpenam-4-carboxylic acid. The 2-vinylpenam is deacylated by known methods to provide the 2-vinylpenam nucleus, 6β-amino-2β-methyl-2α-vinylpenam-4-carboxylic acid. The nucleus or an ester thereof is N-acylated with a carboxylic acid, e.g., phenylacetic acid or α-aminophenylacetic acid, to provide a 6β-acylamino-2β-methyl-2α-vinylpenam-4-carboxylic acid antibiotic compound.

DETAILED DESCRIPTION

The enzymatic process of this invention comprises incubating with isopenicillin N synthetase in an aqueous medium in the presence of oxygen and ferrous ion at a temperature between about 20° C. and about 40° C. and a pH of between about 6 and about 9, a tripeptide of the formula A

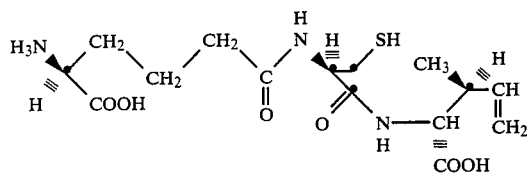

or an alkali metal or alkaline earth metal salt thereof to form a 2-vinyl-2-methylpenam of the formula

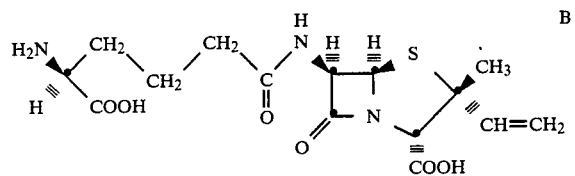

or an alkali metal or alkaline earth metal salt thereof.

The salts referred to above are e.g. the sodium, potassium, and calcium salts. The tripeptide substrate is generally used at concentrations of up to about 5 mmolar, e.g., from about 0.1 mmolar to about 5 mmolar. The tripeptide is difficult to prepare and maintain in the free thiol form since it readily oxidizes to the stable disulfide. The disulfide is reduced to the thiol prior to use in the process with a reducing agent such as dithiolthreitol, β-mercaptoethanol, glutathione, or other suitable agent.

The enzyme is preferably used in large excess relative to the amount of substrate. Such excess amounts are readily determined by the enzymatic activity of the particular IPNS preparation. The activity of the enzyme is expressed in terms of units of activity with a unit of activity equal to the activity per ml required to convert 1 μM/ml. of substrate to product.

For best results, purified enzyme, such as that described by Pang et al., *Biochem. J.* (1984), 222, 789–795, and by J. E. Baldwin et al., *FEBS LETTER*, 1985, 188, 253, is used in the process.

The process also can be carried out with less pure enzyme preparations from various sources, for example, cell free extracts of the enzyme prepared according to Hollander et al., *Science*, 224, 610–612, from *Cephalosporium acremonium* ATCC 48272; or from cultures of *Penicillium chrysogenum, Aspergillus nidulans, Streptomyces lipmanii* and *Streptomyces clavuligerus*. Preferably, the enzyme is purified.

The process is carried out in the presence of ferrous ion and ascorbic acid. With these cofactors present, the enzyme, which functions as an oxidase, provides its maximum activity. The minimum amount of ferrous ion required to activate the enzyme is generally used. Usually, the concentration of the ferrous ion is between abut 50 μM and about 0.2 μM. The higher the purity of the IPNS enzyme, the lower the concentration of ferrous ion required for activation. Conversely with semi-purified enzyme, higher concentrations of ferrous ion are required. Ferrous ion is most activating when used in conjunction with ascorbic acid. Generally, ascorbic acid is used in concentration equal to or greater than the $Fe^{2+}$ concentration. Sources of ferrous ion include ferrous salts of sufficient water solubility to achieve the desired concentration in the aqueous incubation mixture. Such salts as ferrous sulfate, ferrous chloride, ferrous carbonate or other suitable $Fe^{2+}$ sources can be used.

During the process, hydrogen peroxide may be generated. A catalase, such as beef liver catalase, is added to the incubation mixture to avoid any excess levels of peroxide. High levels of peroxide can have a deleterious effect on the enzyme or substrate.

The process is carried out in the presence of oxygen and with agitation of the incubation mixture by shaking or stirring. Sufficient oxygen is supplied by carrying out the process in a reaction vessel open to the air. However, when the process is carried out with high concentrations of substrate and a large excess of enzyme, it may be beneficial to introduce oxygen into the incubation mixture during the process.

The process proceeds rapidly when an excess of purified enzyme is used. In general, the process can be complete in about 10 minutes to about 2 hours and, preferably, is allowed to proceed for 45 minutes to an hour. It will be appreciated that with incubations of substrate and enzyme on a large scale, somewhat longer times may be required for completion of the process.

The incubation mixture is maintained at a pH between about 6 and about 9 and, preferably, pH 7.5 to 8.5 with a buffer. Suitable buffers include ammonium bicarbonate, tris buffer and MOPS (3-[N-morpholino]propanesulfonic acid.

The process can be carried out at a temperature between about 20° C. and about 40° C. and, preferably, between about 25° C. and about 30° C.

The process is terminated by adding to the reaction mixture a water miscible organic solvent such as acetone. The protein which precipitates is separated, e.g., by centrifugation, and the product is isolated from the supernatant by conventional means. For example, the supernatant can be lyophilized and the product isolated from the lyophile by chromatography such as reverse phase HPLC. Alternatively, the product may be isolated by extracting the incubation mixture after separation of protein.

The substrate tripeptide A used in the process, δ-(L-α-aminoadipoyl)-L-cysteinyl-D-γ,δ-didehydroisoleucine, is prepared in the following manner. First, 2-(t-butyloxycarbonylamino)-3-methylpent-4-eneoic acid (prepared according to the method of P. A. Bartlett and J. F. Barstow, *J. Org. Chem.*, 1982, 47, 3933) is esterified with benzyl bromide and sodium bicarbonate. The benzyl ester is treated with formic acid to remove the t-BOC amino-protecting group to provide the amino ester, benzyl 2-amino-3-methylpent-4-eneoate, as the formate salt as shown below.

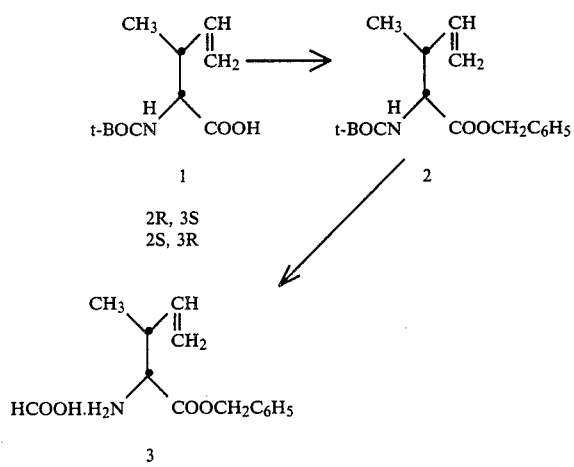

The formate salt 3 is then coupled with the amino-protected and esterified dipeptide δ-(L-α-aminoadipoyl)-L-cysteine represented by the formula 4

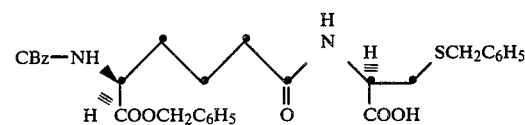

wherein CBz is benzyloxycarbonyl.

The coupling is carried out by employing the EEDQ method described by J. E. Baldwin et al., *J. Chem. Soc., Perkin* 1, 1981, 2253, and provides a 1:1 mixture of the diastereoisomers represented by the following formulae 5 and 6

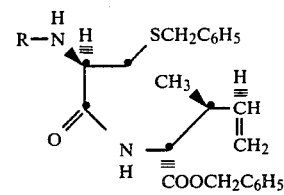

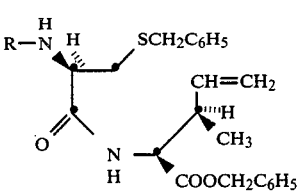

wherein R is the CBz and benzyl ester-protected δ-(L-α-aminoadipoyl)acyl group of 4.

The diastereoisomers 5 and 6 are separated by chromatography, e.g., plate layer chromatography on silica gel using ethyl acetate:hexane (4:6) as the eluant. The isomer 5 is deprotected with sodium in liquid ammonia by following the procedures described by J. E. Baldwin et al., *J. Chem. Soc., Perkin* 1, 1981, 2253. Under these conditions both benzyl ester groups, the S-benzyl group and the CBz group, are removed to provide the free thiol represented by the formula A shown in zwitterionic form.

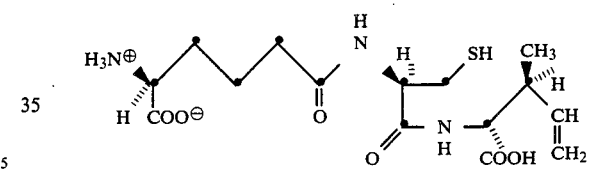

The thiol A tends to readily oxidize to the dithio compound which is highly stable and a preferred form for storage prior to use in the process. Accordingly, the thiol A is converted to the disulfide with oxygen gas in dilute ammonium hydroxide solution at pH 8. The disulfide of A can be purified by preparative electrophoresis (pH 3.5, 4 KV, 80 minutes) with extraction of the ninhydrin active band that migrates about 5–10 cm towards the anode.

The 2-methyl-2-vinylpenam obtained in the process, 6β-(L-α-aminoadipoylamino)-2α-methyl-2α-vinylpenam-3-carboxylic acid exhibits about 85% of the antibacterial activity of isopenicillin N against *Staphylococcus aureus* N.C.T.C. 6571 and *Sarcina lutea* D.S. 292.

The 2-vinylpenam product also can be converted to 6β-acylamino-2β-methyl-2-vinylpenam-3-carboxylic acids via deacylation of the α-aminoadipoyl group and reacylation of the 6-amino-2-methyl-2-vinylpenam nucleus. Thus, according to one of its aspects, this invention provides 6β-acylamino-2β-methyl-2-vinylpenam-3-carboxylic acids represented by the formula C.

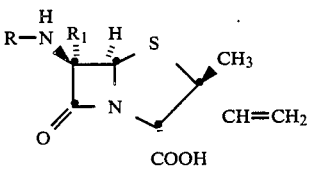

wherein R is α-aminoadipoyl or an acyl group represented by the formula

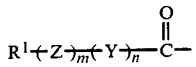

wherein $R^1$ is a phenyl group represented by the formula

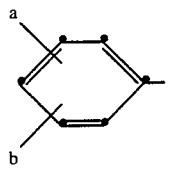

wherein a and b independently are hydrogen, hydroxy, halogen, $C_1-C_4$ alkyl, $C_1-C_4$ alkoxy, amino, $C_1-C_4$ alkylsulfonylamino, carboxy, carbamoyl, carboxymethyl, hydroxymethyl, aminomethyl or trifluoromethyl; Z is O or S, Y is a straight or branched chain divalent $C_1-C_4$ alkylene radical and m and n are 0 or 1; or $R^1$ is cyclohexenyl or cyclohexadienyl; or R is a heteroalkanoyl group represented by the formula

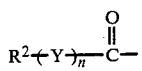

wherein $R^2$ is thienyl, furyl, benzothienyl, benzofuryl, thiazolyl, oxazolyl, thiadiazolyl, oxadiazolyl and such heterocycles substituted by $C_1-C_4$ alkyl, $C_1-C_4$ alkoxy, hydroxy, amino or halogen; an isoxazolyl group represented by the formula

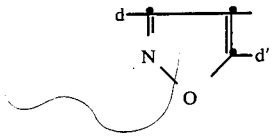

wherein d and d' independently are $C_1-C_4$ alkyl, phenyl, halophenyl or hydroxyphenyl; and Y and n have the same meanings as defined above; or R is an acyl group

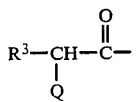

wherein $R^3$ is $R^1$ or $R^2$ as defined above and Q is hydroxy, $C_1-C_4$ alkanoyloxy, carboxy, sulfo, amino or a substituted amino group represented by the formulae

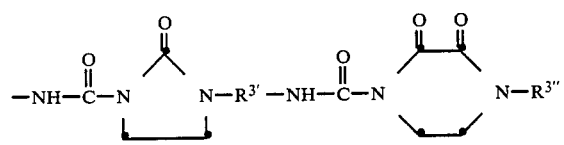

wherein $R^{3'}$ is hydrogen, $C_1-C_4$ alkanoyl or $C_1-C_4$ alkylsulfonyl and $R^{3''}$ is $C_1-C_4$ alkyl or benzyl; or R is a cyclic acyl group represented by the formula

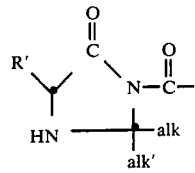

wherein $R^1$ has the same meanings as defined above and alk and alk' independently are $C_1-C_3$ alkyl; or R is an oximino-substituted acyl group represented by the formula

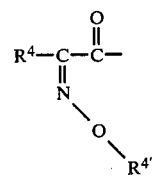

wherein $R^4$ is $R^1$ or $R^2$ as defined above and $R^{4'}$ is a straight or branched chain $C_1-C_6$ alkyl radical or substituted $C_1-C_6$ alkyl radical substituted by hydroxy, amino, carboxy, carbamoyl, N,N-di($C_1-C_4$ alkyl)carbamoyl or cyano; $R_1$ is hydrogen, $C_1-C_4$ alkoxy, $C_1-C_4$ alkylthio or formamido; and the pharmaceutically acceptable, non-toxic salts thereof.

In the above definition of the 2-vinylpenams C, the term $C_1-C_4$ alkyl refers to methyl, ethyl, n-propyl, isopropyl, n-butyl, t-butyl and the like; $C_1-C_4$ alkoxy refers to methoxy, ethoxy, isopropoxy, t-butoxy, isobutoxy and the like; $C_1-C_4$ alkanoyl refers to acetyl, propionyl, butyryl and the like; $C_1-C_4$ alkylthio refers to methylthio, ethylthio, n-butylthio, isopropylthio and the like; $C_1-C_4$ alkanoyloxy refers to acetoxy, propionoxy, butyryloxy and the like; $C_1-C_4$ alkylsulfonyl refers to methylsulfonyl, ethylsulfonyl, n-butylsulfonyl and the like; and halogen refers to fluoro, chloro, bromo and iodo.

Examples of 6β-acyl groups when R is a group represented by the formula

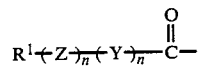

and m and n=0 are benzoyl, 4-hydroxybenzoyl, 4-ethoxybenzoyl, 2,6-dimethoxybenzoyl, 4-chlorobenzoyl, 3-methylsulfonylaminobenzoyl, 4-trifluoromethylbenzoyl and 3,4-dimethylbenzoyl. When m is 0 and n is 1, examples of such acyl groups are phenylacetyl, 4-hydroxyphenylacetyl, 4-chlorophenylacetyl, 3,4-dichlorophenylacetyl, 3-ethoxyphenylacetyl, 2-fluorophenylacetyl, 2-aminomethylphenylacetyl, 4-trifluoromethylphenylacetyl, 3-carbamoylphenylacetyl, 4-aminophenylacetyl, 3-(ethylsulfonylamino)phenylacetyl, 4-carboxyphenylacetyl, 4-hydroxy-3-ethoxyphenylacetyl, 4-(carboxymethyl)phenylacetyl, 4-ethylphenylacetyl, 3,4-dimethoxyphenylacetyl, α-phenylpropionyl and α-phenylbutyryl. When m and n are 1, examples of such acyl groups are phenoxyacetyl, α-phenoxypropionyl, 4-chlorophenoxyacetyl, 4-methoxyphenoxyacetyl, 3-hydroxymethylphenoxyacetyl, 3-fluorophenoxyacetyl, 3-carboxyphenoxyacetyl, 4-hydroxyphenoxyacetyl, phenylthioacetyl, 2-(phenylthio)propionyl, 4-chlorophenylthioacetyl, 3,4-dichlorophenylthioacetyl, 3-methylphenylthioacetyl, 3,5-dichlorophenylthioacetyl, 4-fluorophenylthioacetyl, 3-hydroxyphenylthioacetyl, 4-isopropoxyphenylthioacetyl and 4-aminomethylphenylthioacetyl.

Examples of heteroalkanoyl acyl groups when R is

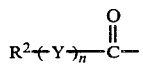

and n is 1 are 2-thienylacetyl, 2-furylacetyl, benzothien-2-ylacetyl, benzofurylacetyl, α-(2-thienyl)propionyl, β-(2-thienyl)propionyl, 2-methyl-1,3,4-thiadiazol-5-ylacetyl, 2-ethylthiazol-4-ylacetyl, 2-aminooxazol-4-ylacetyl, 2-amino-1,3,4-oxadiazol-5-ylacetyl, 3-phenyl-5-methylisooxazol-4-ylacetyl, 3-(2,6-dichlorophenyl)-5-methylisoxazole-4-ylacetyl and 5-ethylisoxazol-4-ylacetyl; and when n is 0, 2-thienoyl, 2-furoyl, benzothien-2-oyl, 3-(2-chlorophenyl)-5-methylisoxazol-4-oyl, 3-(2,6-dichlorophenyl)-5-methylisoxazol-4-oyl and 3-(2-chloro-6-fluorophenyl)-5-methylisoxazol-4-oyl.

Examples of acyl groups when R is the group R³CH(Q)CO— and Q is hydroxy are 2-hydroxy-2-phenylacetyl, 2-hydroxy-2-(2-thienyl)acetyl, 2-hydroxy-2-(4-chlorophenyl)acetyl, 2-hydroxy-2-(3-hydroxyphenyl)acetyl, 2-hydroxy-2-(3-phenyl-5-methylisoxazol-4-yl)acetyl, 2-hydroxy-2-(2-aminothiazol-4-yl)acetyl, 2-hydroxy-2-(4-methoxyphenyl)acetyl and 2-hydroxy-2-(2-methyl-1,3,4-thiadiazol-5-yl)acetyl; and when Q is $C_1$-$C_4$ *L alkanoyloxy*, examples include 2-formyloxy-2-phenylacetyl, 2-acetoxy-2-phenylacetyl, 2-propionoxy-2-(4-hydroxyphenyl)acetyl, 2-acetoxy-2-(2-thienyl)acetyl, 2-acetoxy-2-(2-aminothiazol-4-yl)acetyl and 2-butyryloxy-2-(3,4-dichlorophenyl)acetyl; and when Q is carboxy or sulfo, examples include 2-carboxy-2-phenylacetyl, 2-carboxy-2-(2-thienyl)acetyl, 2-carboxy-2-(2-furyl)acetyl, 2-carboxy-2(4-aminophenyl)acetyl, 2-carboxy-2-(2-aminothiazol-4-yl)acetyl, 2-sulfo-2-phenylacetyl, 2-sulfo-2-(3-carboxyphenyl)acetyl, 2-sulfo-2-(3-thienyl)acetyl, 2-carboxy-2-(2-ethyl-1,3,4-oxadiazol-5-yl)acetyl, 2-sulfo-2-(4-fluorophenyl)acetyl and 2-carboxy-2-(4-hydroxymethylphenyl)acetyl; and when Q is amino, examples of such acyl groups included are 2-amino-2-phenylacetyl; 2-amino-2-(4-hydroxyphenyl)acetyl, 2-amino-2-(3-chloro-4-hydroxyphenyl)acetyl, 2-amino-2-(2-thienyl)acetyl, 2-amino-2-(2-furyl)acetyl, 2-amino-2-(benzothien-2-yl)acetyl, 2-amino-2-(2aminothiazol-4-yl)acetyl, 2-amino-2-(3-phenyl-5-methylisoxazol-4-yl)acetyl, 2-amino-2-(1,4-cyclohexadienyl)acetyl and 2-amino-2-(2-methyl-1,3,4-oxadiazol-5-yl)acetyl; and when Q is a substituted amino group, such 6β-acyl groups are exemplified by 2-[(3-acetylimidazolidin-2-one-1-yl)carbonylamino]-2-phenylacetyl, 2-[(3-methylsulfonylimidazolidin-2-one-1-yl)carbonylamino]-2-(4-hydroxyphenyl)acetyl, 2[(4-ethylpiperazin-2,3-dione-1-yl)carbonylamino]-2-phenylacetyl and 2-amino-2-[(3-ethylimidazolidin-2-one-1-yl)carbonylamino]-2-(2-thienyl)acetyl.

Examples of cyclic acyl groups represented by R in the formula 1 are 2-phenyl-5,5-dimethylimidazolidin-3-one-1-ylcarbonyl and 2-(4-hydroxyphenyl)-5,5-dimethylimidazolidin-3-one-1-ylcarbonyl.

Examples of oximino-substituted acyl groups represented by R are 2-phenyl-2-methoxyiminoacetyl, 2-(2-furyl)-2-(carboxymethoxyimino)acetyl, 2-(2-aminooxazol-4-yl)-2-(carbamoylmethoxyimino)acetyl, 2-(2-aminothiazol-4-yl)-2-methoxyiminoacetyl, 2-(2-aminothiazol-4-yl)-2-(2-carboxyprop-2-oxyimino)acetyl and 2-(2-aminothiazol-4-yl)-2-(N,N-dimethylcarbamoylmethoxyimino)acetyl.

Preferred 2-vinylpenam compounds of the invention are represented by the formula C where R is an acyl group R³—CH(Q)CO— and R₁ is hydrogen, in particular, wherein R³ is phenyl or substituted phenyl and Q is amino or a subsituted amino group as defined above.

A further preferred group of 2-vinylpenams of this invention are represented when R is an oximinosubstituted acyl group

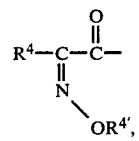

in particular, penams having the oximino group in the syn or Z form.

The 2-vinylpenams of the invention form pharmaceutically acceptable salts with suitable bases. Such salts include, e.g., the sodium, potassium, calcium and amine salts. Amine salts formed with amines such as the primary, secondary and tertiary amines, e.g., ethylamine, diethylamine, tri-n-butylamine, benzylamine, dibenzylamine, cyclohexylamine, ethanolaine, di-ethanolamine, dipropanolamine and procaine.

Likewise, pharmaceutically acceptable acid addition salts can be formed with compounds represented by the formula C wherein the acyl group R bears an amino group substituent. For example, the amino group of 6β-phenylglycylamino-2-methyl-2-vinylpenam-3-carboxylic acid (formula 1, R=R³CH(Q)CO— and R³=C₆H₅, Q=NH₂) can form the corresponding hydrochloride salt.

The pharmaceutically acceptable salts are useful forms of the 2-vinylpenam antibiotics which can be employed in formulations of the antibiotics for administration.

The 2-vinylpenam antibiotics are prepared via N-deacylation of the α-aminoadipoyl-2-vinylpenam represented by the above formula B. The deacylation is carried out in known manner by the process described by Weissenburger et al., U.S. Pat. No. 3,499,909. The product of the deacylation, 6β-amino-2α-vinyl-2β-methylpenam-3α-carboxylic acid, is represented by the formula D

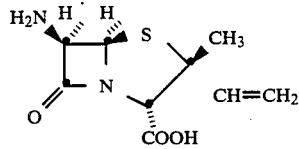

The 6β-amino nucleus D is then reacylated to provide a 2-vinylpenam of the formula C wherein R₁ is hydrogen. The acylation is carried out by the known coupling methods used for the N-acylation of 6-aminopenicillanic acid. For example, the acylating acid is converted to an active derivative such as an acid halide, acid azide, active ester, anhydride or the like, and the active derivative used to acylate the 6β-amino nucleus. For example, phenylacetyl chloride is coupled with D in an inert solvent in the presence of an acid-binding agent such as sodium carbonate or triethylamine. Active esters which can be used include those formed with the acid and an N-hydroxyheterocycle such as hydroxybenztriazole and hydroxysuccinimide; or the anhydrides formed with a haloformate such as ethyl chloroformate and isobutyl chloroformate.

During the acylation, the 3-carboxy group of D may be protected by esterification, e.g., with a conventional carboxy-protecting ester group. Conventional carboxy-protecting groups such as benzhydryl, p-nitrobenzyl, p-methoxybenzyl, benzyl, trialkylsilyl, e.g., trimethylsilyl and like temporary protecting groups can be used.

In a further aspect, this invention provides the 6β-amino-2α-vinyl-2β-methylpenam-3α-carboxylic acid represented by the formula D, the carboxy-protecting esters and salts thereof. Carboxy-protecting ester derivatives of the nucleus D are the esters formed with conventional carboxy-protecting esters used in the penicillin art for the temporary protection of the $C_3$ carboxy group. Such ester groups are exemplified by t-butyl, allyl, haloalkyl such as 2,2,2-trichloroethyl and 2-iodoethyl, arylmethyl such as benzyl, diphenylmethyl, p-methoxybenzyl and p-nitrobenzyl, trialkylsilyl such as trimethylsilyl and t-butyldiethylsilyl and like groups. Other commonly used carboxy-protecting groups are described by E. Haslam in *Protective Groups In Organic Chemistry*, J. F. W. McOmie, Ed., Plenum Press, New York, NY, 1973, chapter 5, and by T. W. Greene in *Protective Groups in Organic Synthesis*, John Wiley & Sons, New York, NY, 1981, chapter 5.

The salts of the nucleus D are the acid addition salts formed with an acid and the 6-amino group, and the 3-carboxy group salts. Carboxy group salts are formed with suitable bases and include the sodium, potassium, calcium and like salts. The acid addition salts are formed with mineral acids such as hydrochloric acid, hydrobromic acid and sulfuric acid, and with the sulfonic acids such as p-toluenesulfonic acid and benzenesulfonic acid.

The 6β-acylamino-6α-alkoxy-2α-vinyl-2β-methylpenam-3α-carboxylic acids represented by the formula C wherein $R_1$ is $C_1$–$C_4$ alkoxy are prepared by the method described by U.S. Pat. No. 4,044,000. The 2-vinylpenams wherein $R_1$ is formamido can be obtained by the method described by U.S. Pat. No. 4,539,149.

The 2-vinylpenams provided herein are useful antibiotics which inhibit the growth of microorganisms pathogenic to man and animals. For example, they inhibit the growth of gram-positive bacteria such as staphylococcus and streptococcus. The 2-vinylpenams or pharmaceutically acceptable non-toxic salts thereof may be used in treating infections by the methods employed for the use of other penicillin antibiotics such as penicillin V or ampicillin. For example, the 2-vinylpenams may be administered parenterally or orally in antibiotically effective amounts.

The following Examples further describe the invention.

EXAMPLE 1

Preparation of δ-(L-α-aminoadipoyl)-L-cysteinyl-D-γ,δ-didehydroisoleucine

A. Benzyl 2-(t-butyloxycarbonylamino)-3-methylpent-4-enoate

A mixture of 4.4 mmol of 2-(t-butyloxycarbonylamino)-3-methylpent-4-enoic acid (2R,3S; 3S,2R) prepared by the method of P. A. Bartlett et al., *J. Org. Chem.*, 1982, 47, 3933, in 10 ml. of dry DMF containing 4.4 mmol of benzyl bromide, 4.4 mmol of sodium bicarbonate and 10 mg. of sodium iodide was stirred for 15 minutes at 20° C. The mixture was dissolved in ethyl acetate, the solution washed three times with water, was dried over sodium sulfate, filtered and evaporated. The ester product was purified by flash chromatography on silica gel. The ester was obtained in an 80% yield as an oil.

NMR (300 MHz, $C^2HCL_3$): δ1.01 (3H, d, J 6 Hz, 3—$CH_3$), 1.44 (9H, s, t-butyl), 2.58–2.71 (1H, m, 3—H), 4.32–4.40 (1H, m, 2—H), 5.01–5.27 (5H, m, 5—H, NH, $CH_2C_6H_5$), 5.05–5.37 (1H, m, 4—H), 7.33–7.41 (5H, m, $C_6H_5$—H).

IR ($CHCl_3$ solution): γmax 3005 m, 1730 s ($CO_2$), 1710 s ($CO_2$), 1600 w, 1502 m, 1205 s, 1160 m.

m/e ($NH_3$, Desorption Chemical Ionization): 320 ($MH^+$, 100%).

B. Benzyl 2-amino-3-methylpent-4-eneoate formic acid salt

The benzyl ester (step A), 0.40 mmol, was dissolved in 1 ml. of formic acid and the solution stirred for 2 hours at 20° C. The solution was evaporated to yield the crude formic acid salt which was used in the next step without further purification.

C. The benzyl ester formic acid salt (step B) was coupled with the protected α-aminoadipoyl-L-cysteinyl dipeptide represented by the formula

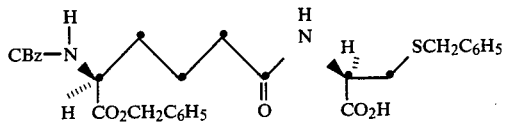

using the standard coupling conditions with EEDQ as described by J. E. Baldwin et al., *J. Chem. Soc. Perkin 1*, 1981, 2253. The S-benzyl, CBz-protected title tripeptide dibenzyl ester was obtained in 50% yield as a 1:1 mixture with the corresponding diastereoisomer, the allo-isoleucinyl tripeptide.

The protected title tripeptide was separated from the diastereoisomeric mixture by plate layer chromatography on silica gel using ethyl acetate:hexane, 4:6, v:v as eluant. The protected title tripeptide was crystallized to homogeneity from ethyl acetate:hexane and melted at 116° C. to 118° C.

IR ($CHCl_3$): γmax 1730 s ($CO_2$), 1700 s ($CO_2$), 1508 m, 1378 m, 1205 w.

NMR (300 MHz, $C^2HCl_3$): δ1.00 (3H, d, J=6 Hz, $CHCH_3$), 1.61–1.92 (4H, m, $CH_2$—$CH_2$—$CH_2CO$), 1.07–1.25 (3H, m, $Ch_2$—CO, $CHCH_3$), 2.58–2.88 (2H, m, $CH_2S$), 3.75 (2H, s, $SCH_2C_6H_5$), 4.36–4.48 (2H, m, 2×NHCHCO), 4.57–4.63 (1H, m, NHCHCO), 4.99–5.21 (8H, m, 3×$OCH_2C_6H_5$, C=$CH_2$), 5.56–5.75 (2H, m, CH=$CH_2$, NH), 6.35 (1H, d, J=8 Hz, NH), 6.91 (1H, d, J=8.5 Hz, NH), 7.31–7.37 (20H, m, aryl H).

m/e (field desorption) 779 ($M^+$).

The structure of the separated title compound was further shown by its reduction in benzene for one hour with hydrogen at 1 atmosphere using [($C_6H_5$)$_3$P]$_3$RhCl, to the corresponding allo-isoleucinyl tripeptide described by J. E. Baldwin et al., *J. Chem. Soc., Chem. Commun.*, 1984, 1167, and references cited therein.

D. Deprotection of title tripeptide

The N-CBz S-benzyl protected tripeptide dibenzyl ester (step C) was deprotected in sodium/liquid ammonia under the conditions described by J. E. Baldwin et al., *J. Chem. Soc.*, Perkin 1, 1981, 2253, to provide the title tripeptide.

The deprotected tripeptide was then oxidized to the disulfide in dilute ammonium hydroxide, pH 8, by passing oxygen gas through the solution for 2 hours. The disulfide was purified by preparative electrophoresis (pH 3.5, 4 KV, 80 minutes) and by extracting the ninhydrin-active band that migrated 5-10 cm towards the anode. The purified disulfide was obtained in 77% yield.

NMR (300 MHz, D$_2$O, HOD=4.63 p.p.m.): δ0.87 (3H, d, J=5.5 Hz, CHC$\underline{H}$$_3$), 1.51-1.74 (4H, m, C$\underline{H}$$_2$C$\underline{H}$$_2$CH$_2$CO), · 2.08-2.26 (2H, m; CH$_2$CO), 2.55-2.57 (1H, m, C$\underline{H}$CH$_3$), 2.77-3.03 (2H, m, CH$_2$S), 3.47-3.58 (1H, m, N$\underline{H}$CHCO), 4.14 (1H, d, J=5.5 Hz, NHC$\underline{H}$CO), 4.91-4.96 (2$\underline{H}$, m, C=CH$_2$), 5.60-5.67 (1H, m, C$\underline{H}$=CH$_2$).

m/$\overline{e}$ (positive argon F.A.B., in presence of dithiothreitol) 376 (MH$^+$, 12%).

EXAMPLE 2

6β-(L-α-Aminoadipoyl)-2β-methyl-2α-vinylpenam-3-carboxylic acid

An aqueous solution of the δ-(L-α-aminoadipoyl)-L-cysteinyl-D-γ,δ-didehydroisoleucine disulfide prepared as described by Example 1 (28 mM, 0.100 ml.) was mixed with aqueous solutions of dithiothreitol (100 mM, 0.100 ml.), L-ascorbic acid (50 mM, 0.100 ml.), ferrous sulfate (5 mM, 0.100 ml), bovine liver catalase (10,000 units/ml., 0.050 ml.) and ammonium bicarbonate (50 mM, 3.5 ml.). The pH of the mixed solutions was monitored and, when necessary, adjusted to 8 by adding dilute sodium hydroxide (100 mM). The mixed solutions were shaken at 27° C. for 5 minutes and an isopenicillin N synthetase preparation isolated from *Cephalosporium acremonium* (5 I.U./ml., 1 ml.) in a 50 mM solution of ammonium carbonate was added. The incubation mixture was shaken in two 10 ml. vials at 27° C. for 45 minutes and then the reaction was terminated by precipitating the protein with 7 ml. of acetone. The precipitate was separated by centrifugation. The supernatant was evaporated in vacuo to remove the acetone and the residue was freeze-dried to yield the crude 2α-vinylpenam represented by the formula

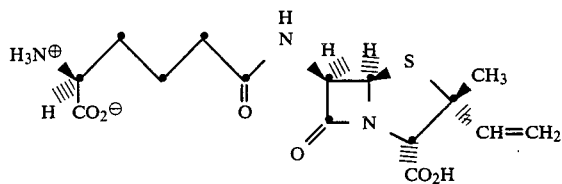

The crude product was purified via reverse phase octadecylsilane HPLC (250×4.6 mm column); mobile phase: 10 mmolar aqueous ammonium bicarbonate; flow 1 ml. min.$^{-1}$; retention time=7-8 minutes.

NMR (500 MHz, D$_2$O, 3-trimethylsilylpropionate [2,2,3,3—$^2$H$_4$] TSP=0.00 p.p.m.): δ1.53-1.77 (4H, m, C$\underline{H}$$_2$C$\underline{H}$$_2$CH$_2$CO), 1.59 (3H, s, 3β—CH$_3$), 2.25-2.38 (2H, m, C$\underline{H}$$_2$CO), 3.56-3.59 (1H, m, CH(CH$_2$)$_3$), 4.18 (1H, s, 2—H), 5.03 (1H, d, J 10.5 Hz, C$\underline{H}$=CH$_2$), 5.22 (1H, d, J 17 Hz, CH=CH$_2$), 5.35, 5.45 (2H, AB̄q, J 4 Hz, 5, 6—H), 5.91 (1H, dd, J10.5, 17 Hz, CH=CH$_2$).

The 2β-methyl group follows from Nuclear Overhauser experiments. Thus, irradiation of the 2β—CH$_3$ group, at δH 1.59, gave enhancement (12%) of 2—H but not of 5—H, whereas irradiation of the CH=CH$_2$ proton, at δH 5.91, gave enhancement of 5—$\underline{H}$ (3%).

m/e (positive argon fast atom bombardment) 372 (MH$^+$).

EXAMPLE 3

6β-Amino-2α-vinyl-2β-methylpenam-3-carboxylic acid

6β-(L-α-aminoadipoyl)-2β-methyl-2α-vinylpenam-3-carboxylic acid is converted to the N-phthaloyl derivative and the sodium salt of the derivative is suspended in dry methylene chloride. The suspension is treated with trimethylchlorosilane in the presence of pyridine to form the trimethylsilyl ester. The silyl ester derivative is reacted at about −5° C. with phosphorous pentachloride to form the corresponding imino chloride. The reaction mixture is cooled to about −20° C. and is treated with methyl alcohol to form the corresponding imino ether. The mixture is allowed to warm to about 0° C. and water is added to form the title nucleus compound. The mixture is poured into a cold mixture of water and methyl alcohol and the aqueous layer is separated. After adjustment of the pH to about 4, the solution is allowed to stand at about 5° C. to precipitate the title nucleus compound.

EXAMPLE 4

6β-Phenoxyacetylamino-2α-vinyl-2β-methylpenam-3-carboxylic acid

6β-Amino-2α-vinyl-2β-methylpenam-3-carboxylic acid is acylated in acetone-water with phenoxyacetyl chloride in the presence of sodium carbonate to provide the title compound.

EXAMPLE 5

6β-(D-Phenylglycylamino)-2α-vinyl-2β-methylpenam-3-carboxylic acid

The 2α-vinylpenam nucleus as the t-butyl ester is acylated with the anhydride of D-α-(t-butyloxycarbonylamino)phenylacetic acid formed with methyl chloroformate to form the t-BOC protected 6β-(D-phenylglycylamino)2α-vinyl-2β-methylpenam-3-carboxylic acid t-butyl ester. The title compound is obtained upon treatment of the ester with trifluoroacetic acid-anisole.

EXAMPLE 6

6β-[2-(2-Aminothiazol-4-yl)-2-syn-methoxyiminoacetamido]-2α-vinyl-2β-methylpenam-3-carboxylic acid The 2α-vinylpenam nucleus is acylated with 2-(2-tritylaminothiazol-4-yl)-2-syn-methoxyiminoacetyl chloride and the trityl-protecting group is removed with 98% formic acid to provide the title compound.

I claim:

1. The process for preparing a compound of the formula

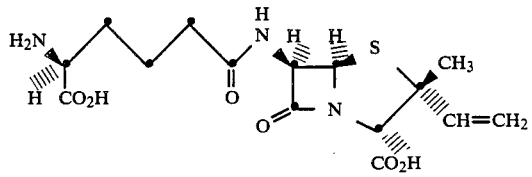

which comprises contacting in an aqueous medium at a temperature between about 20° C. and about 40° C. and at a pH of between about 6 and about 9 in the presence of ferrous ion and ascorbic acid a tripeptide of the formula

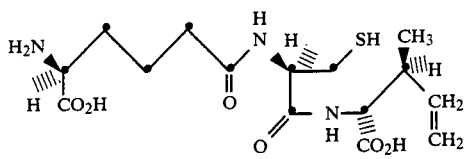

with isopenicillin N synthetase.

2. The process of claim 1 wherein the temperature is between about 25° C. to about 35° C. and the pH is between about 7 and about 8.

3. The process of claim 1 wherein the isopenicillin N synthetase is purified enzyme.

4. A compound of the formula

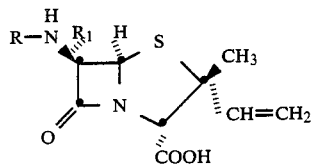

wherein R is α-aminoadipoyl or an acyl group of the formula

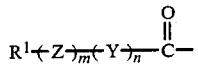

wherein $R^1$ is a phenyl group of the formula

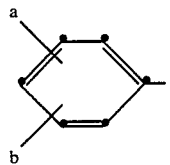

wherein a and b independently are hydrogen, hydroxy, halogen, $C_1$-$C_4$ alkyl, $C_1$-$C_4$ alkoxy, amino, $C_1$-$C_4$ alkylsulfonylamino, carboxy, carbamoyl, carboxymethyl, hydroxymethyl, aminomethyl or trifluoromethyl; Z is O or S, Y is a straight or branched chain divalent $C_1$-$C_4$ alkylene radical and m and n are 0 or 1; or $R^1$ is cyclohexenyl or cyclohexadienyl; or R is a heteroalkanoyl group of the formula

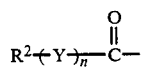

wherein $R^2$ is thienyl, furyl, benzothienyl, benzofuryl, thiazolyl, oxazolyl, thiadiazolyl, oxadiazolyl and the aforesaid heterocycles substituted by $C_1$-$C_4$ alkyl, $C_1$-$C_4$ alkoxy, hydroxy, amino or halogen; an isoxazolyl group of the formula

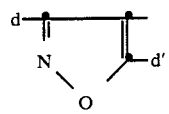

wherein d and d' independently are $C_1$-$C_4$ alkyl, phenyl, halophenyl or hydroxyphenyl; and Y and n have the same meaning as defined above; or R is an acyl group

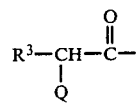

wherein $R^3$ is $R^1$ or $R^2$ as defined above and Q is hydroxy, $C_1$-$C_4$ alkanoyloxy, carboxy, sulfo, amino or a substituted amino group of the formula

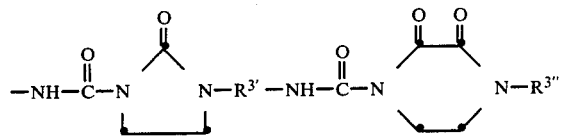

wherein $R^{3'}$ is hydrogen, $C_1$-$C_4$ alkanoyl or $C_1$-$C_4$ alkylsulfonyl and $R^{3''}$ is $C_1$-$C_4$ alkyl or benzyl; or R is a cyclic acyl group of the formula

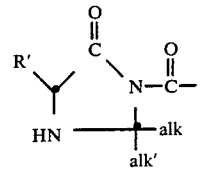

wherein $R^1$ has the same meanings as defined above and alk and alk' independently are $C_1$-$C_3$ alkyl; or R is an oximino-substituted acyl group of the formula

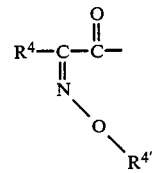

wherein $R^4$ is $R^1$ or $R^2$ as defined above and $R^{4'}$ is a straight or branched chain $C_1$-$C_6$ alkyl radical or substituted $C_1$-$C_6$ alkyl radical substituted by hydroxy, amino, carboxy, carbamoyl, N,N-di($C_1$-$C_4$ alkyl)carbamoyl or cyano; $R_1$ is hydrogen, $C_1$-$C_4$ alkoxy, $C_1$-$C_4$ alkylthio or formamido; and the pharmaceutically acceptable, non-toxic salts thereof.

5. The compound of claim 4 wherein R is α-aminoadipoyl.

6. The compound of claim 4 wherein R is an acyl group of the formula

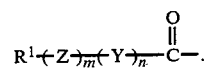

7. The compound of claim 4 wherein R is an acyl group of the formula

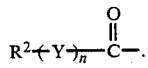

8. The compound of claim 7 wherein $R^2$ is an isoxazolyl group of the formula

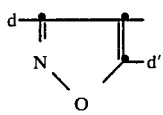

and n is 0.

9. The compound of claim 4 wherein R is an acyl group of the formula

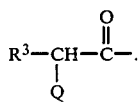

10. The compound of claim 9 wherein $R^3$ is

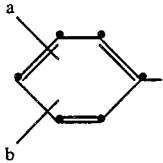

and Q is amino or substituted amino.

11. The compound of claim 4 wherein R is a cyclic acyl group of the formula

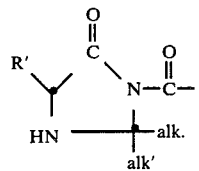

12. The compound of claim 4 wherein R is an oximino-substituted acyl group of the formula

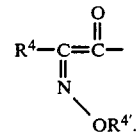

13. The compound of claim 12 wherein $R^4$ is 2-aminothiazol-4-yl or 2-aminooxazol-4-yl and $R^{4'}$ is $C_1$–$C_6$ alkyl or carboxy-substituted $C_1$–$C_6$ alkyl.

14. A compound of the formula

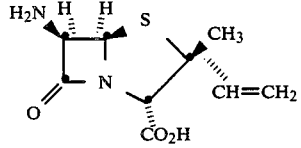

and the carboxy-protecting esters and salts thereof.

* * * * *